United States Patent [19]

Dextraze

[11] Patent Number: 4,880,922
[45] Date of Patent: Nov. 14, 1989

[54] CARBAPENEMS WITH QUATERNIZED HETEROTHIOALKYLTHIO SUBSTITUTION AT POSITION 2

[75] Inventor: Pierre Dextraze, Quebec, Canada

[73] Assignee: Bristol-Myers Company, New York, N.Y.

[21] Appl. No.: 800,867

[22] Filed: Nov. 22, 1985

[51] Int. Cl.$^4$ .................. C07D 487/04; A01K 31/40
[52] U.S. Cl. .................................................. 540/350
[58] Field of Search .................. 540/350; 514/210

[56]  References Cited
FOREIGN PATENT DOCUMENTS
170073  2/1985  European Pat. Off. ............ 514/210

*Primary Examiner*—Robert Gerstl
*Attorney, Agent, or Firm*—David M. Morse

[57]  ABSTRACT

A novel series of carbapenem derivatives characterized by a 2-substituent of the formula

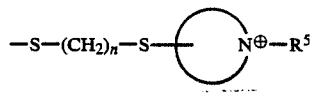

in which n has a value of 1, 2 or 3; $R^5$ represents an optionally substituted aliphatic, cycloaliphatic, cycloaliphatic-aliphatic, araliphatic, heteroaraliphatic, heterocyclyl or heterocyclylaliphatic radical; and

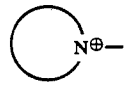

represents a quaternized nitrogen-containing aromatic heterocycle bonded to the group —S—(CH$_2$)n—S— via a ring carbon atom.

5 Claims, No Drawings

4,880,922

CARBAPENEMS WITH QUATERNIZED HETEROTHIOALKYLTHIO SUBSTITUTION AT POSITION 2

FIELD OF THE INVENTION

The present invention is directed to new carbapenem antibiotics in which the 2-substituent has the formula

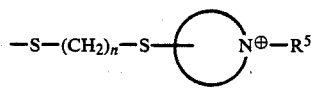

in which n has a value of 1, 2 or 3; $R^5$ represents an optionally substituted aliphatic, cycloaliphatic, cycloaliphatic-aliphatic, araliphatic, heteroaraliphatic, heterocyclyl or heterocyclyl-aliphatic radical; and

represents a nitrogen-containing aromatic heterocycle attached to the group —S—$(CH_2)_n$—S— at a ring carbon atom and quaternized by substituent $R^5$.

DESCRIPTION OF THE PRIOR ART

A number of β-lactam derivatives containing the carbapenem nucleus

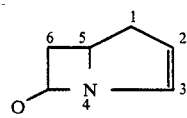

have been disclosed in the literature. These carbapenem derivatives have been reported to possess utility as antibacterial agents and/or β-lactamase inhibitors.

British patent application GB 2 128 187A discloses carbapenem derivatives characterized by a 2-substituent of the formula

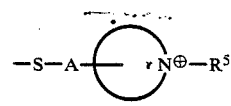

in which A represents a $C_1$-$C_6$ straight or branched chain alkylene group; $R^5$ represents an optionally substituted aliphatic, cycloaliphatic, cycloaliphatic-aliphatic, aryl, araliphatic, heteroaryl, heteroaraliphatic, heterocyclyl or heterocyclyl-aliphatic radical and

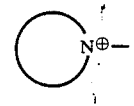

represents a nitrogen-containing aromatic heterocycle attached to the alkylene group A at a ring carbon atom and quaternized by substituent $R^5$. Such derivatives are disclosed as being useful as potent antibacterial agents.

SUMMARY OF THE INVENTION

The present invention provides a novel series of carbapenem derivatives characterized by a 2-substituent of the formula

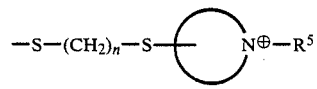

in which n has a value of 1, 2 or 3; $R^5$ represents an optionally substituted aliphatic, cycloaliphatic, cycloaliphatic-aliphatic, araliphatic, heteroaraliphatic, heterocyclyl or heterocyclylaliphatic radical; and

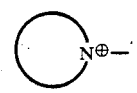

represents a quaternized nitrogen-containing aromatic heterocycle bonded to the group —S—$(CH_2)_n$—S— via a ring carbon atom. More specifically, the present invention provides carbapenem derivatives of the formula

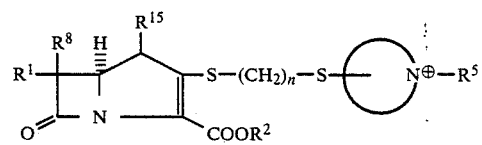

wherein $R^8$ is hydrogen and $R^1$ is selected from the group consisting of hydrogen; substituted and unsubstituted: alkyl, alkenyl and alkynyl having from 1-10 carbon atoms; cycloalkyl and cycloalkylalkyl, having 3-6 carbon atoms in the cycloalkyl ring and 1-6 carbon atoms in the alkyl moieties; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen or sulfur atoms and the alkyl moieties associated with said heterocyclic moieties have 1-6 carbon atoms; wherein the substituent or substituents relative to the above-named radicals are independently selected from the group consisting of:

$C_1$—$C_6$ alkyl optionally substituted by amino, halo, hydroxy or carboxyl halo

—$OR^3$ $$-OCNR^3R^4 \text{ (with } C=O\text{)}$$

—O
‖
—OCNR³R⁴

O
‖
—CNR³R⁴

—NR³R⁴

$$-\!\!\!\bigg\langle{{NR^3}\atop{NR^3R^4}}$$

-continued

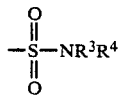

—CO$_2$R$^3$

=O

—SR$^3$

—CN

—N$_3$

—OSO$_3$R$^3$

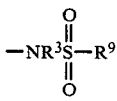

—OP(O)(OR$^3$)(OR$^4$)

—NR$^3$C=NR$^4$

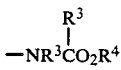

—NO$_2$ wherein, relative to the above-named substituents, the groups R$^3$ and R$^4$ are independently selected from hydrogen; alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; phenyl, aralkyl, aralkenyl and aralkynyl wherein the aryl moiety is phenyl and the aliphatic portion has 1-6 carbon atoms; and heteroaryl, heteroaralkyl, heterocyclyl and heterocyclylalkyl wherein the hetero atom or atoms is the above-named heterocyclic moieties are selected from the group consisting of 1-4 oxygen, nitrogen or sulfur atoms and the alkyl moieties associated with said heterocyclic moieties have 1-6 carbon atoms, or R$^3$ and R$^4$ taken together with the nitrogen to which at least one is attached may form a 5- or 6-membered nitrogen-containing heterocyclic ring; R$^9$ is as defined for R$^3$ except that it may not be hydrogen; or wherein R$^1$ and R$^8$ taken together represent C$_2$-C$_{10}$ alkylidene or C$_2$-C$_{10}$ alkylidene substituted by hydroxy; R$^5$ is selected from the group consisting of substituted and unsubstituted: alkyl, alkenyl and alkynyl, having from 1-10 carbon atoms; cycloalkyl and cycloalkylalkyl, having 3-6 carbon atoms in the cycloalkyl ring and 1-6 carbon atoms in the alkyl moieties; aralkyl, aralkenyl and aralkynyl wherein the aryl moiety is phenyl and the aliphatic portion has 1-6 carbon atoms; heteroaralkyl, heterocyclyl and heterocyclyalkyl wherein the hetero atom or atoms in the above-named heterocyclic moieties are selected from the group consisting of 1-4 oxygen, nitrogen or sulfur atoms and the alkyl moieties associated with said heterocyclic moieties have 1-6 carbon atoms; wherein the above-named R$^5$ radicals are optionally substituted by 1-3 substituents independently selected from:

C$_1$-C$_6$ alkyl optionally substituted by fluoro, chloro carboxyl, hydroxy or carbamoyl; fluoro, chloro or bromo;

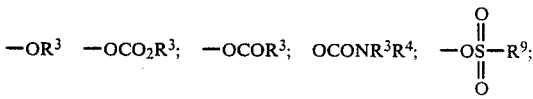

—oxo; —NR$^3$R$^4$; R$^3$CONR$^4$—; —NR$^3$CO$_2$R$^4$;

—NR$^3$CONR$^3$R$^4$; —NR$^3$S—R$^9$; —SR$^3$; —S—R$^9$;

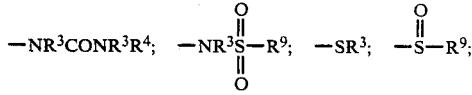

—S—R$^9$; —SO$_3$R$^3$; —CO$_2$R$^3$; —CONR$^3$R$^4$; —CN; or phenyl optionally substituted by 1-3 fluoro, chloro, bromo, C$_1$-C$_6$ alkyl, —OR$^3$, —NR$^3$R$^4$, —SO$_3$R$^3$, —CO$_2$R$^3$ or —CONR$^3$R$^4$, wherein R$^3$, R$^4$, and R$^9$ in such R$^5$ substitutents are as defined above; or R$^5$ may be attached to ⌬N⊕— at another point on the ring so as to form a fused heterocyclic or heteroaromatic ring, which ring may contain additional hetero atoms selected from O, S and N; R$^{15}$ is selected from the group consisting of hydrogen; substituted and unsubstituted: alkyl, alkenyl and alkynyl, having from 1-10 carbon atoms; cycloalkyl, cycloalkylalkyl and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen and sulfur atoms and the alkyl moieties associated with said heterocyclic moieties have 1-6 carbon atoms; wherein the substituent or substituents relative to the above-named radicals are selected from the group consisting of: amino, mono-, di- and trialkylamino, hydroxyl, alkoxyl, mercapto, alkylthio, phenylthio, sulfamoyl, amidino, guanidino, nitro, chloro, bromo, fluoro, cyano and carboxy; and wherein the alkyl moieties of the above-recited substituents have 1-6 carbon atoms; n is an integer of 1, 2 or 3; R$^2$ is hydrogen, an anionic charge or a conventional readily removable carboxyl protecting group, providing that when $R^2$ is hydrogen or a protecting group, there is also present a counter ion; and

represents a substituted or unsubstituted mono-, bi- or polycyclic aromatic heterocyclic radical containing at least one nitrogen in the ring, said ring being attached to S through a ring carbon atom and having a ring nitrogen which is quaternized by the group $R^5$; or a pharmaceutically acceptable salt thereof.

The compounds of formula I are potent antibacterial agents or intermediates useful in the preparation of such agents.

DETAILED DESCRIPTION OF THE INVENTION

The compounds of formula I may be unsubstituted in the 6-position or substituted by substituent groups previously disclosed for other carbapenem derivatives. More specifically, $R^8$ may be hydrogen and $R^1$ may be hydrogen or a non-hydrogen substituent disclosed, for example, in European patent application No. 38,869 (see definition of $R_6$). Alternatively, $R^8$ and $R^1$ taken together may be $C_2$-$C_{10}$ alkylidene or $C_2$-$C_{10}$ alkylidene substituted, for example, by hydroxy.

The compounds of formula I may also be unsubstituted at the 1-position ($R^{15}$=H) or substituted by substituent groups previously disclosed for other carbapenem derivatives. More specifically, $R^{15}$ may be hydrogen or any of the non-hydrogen 1-substituents disclosed for example, in European patent application No. 54,917 (see definition of $R^1$ or $R^2$ therein) or in U.S. Pat. No. 4,350,631. Preferred non-hydrogen $R^{15}$ substituents include $C_1$-$C_6$ alkyl, most preferably methyl; phenyl; and phenyl ($C_1$-$C_6$) alkyl. The non-hydrogen $R^{15}$ substituent may be in either α- or β-configuration, and it is intended that the present invention include the individual α- and β-isomers, as well as mixtures thereof. The most preferred 1-substituted compounds are those having the β-configuration, especially those having the β-methyl substituent.

To elaborate on the definitions for $R^1$, $R^8$ and $R^{15}$:

(a) The aliphatic "alkyl", "alkenyl" and "alkynyl" groups may be straight or branched chain having 1-10 carbon atoms; preferred are 1-6, most preferably 1-4, carbon groups; when part of another substituent, e.g. as in cycloalkylalkyl, or heteroaralkyl or aralkenyl, the alkyl, alkenyl and alkynyl group preferably contains 1-6, most preferably 1-4, carbon atoms.

(b) "Heteroaryl" includes mono-, bi- and polycyclic aromatic heterocyclic groups containing 1-4 O, N or S atoms; preferred are 5- or 6-membered heterocyclic rings such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl, pyrazolyl, etc.

(c) "Heterocyclyl" includes mono-, bi- and polycyclic saturated or unsaturated non-aromatic heterocyclic groups containing 1-4, O, N or S atoms; preferred are 5- or 6-membered heterocyclic rings such as morpholinyl, piperazinyl, piperidyl, pyrazolinyl, pyrazolidinyl, imidazolinyl, imidazolidinyl, pyrrolinyl, pyrrolidinyl, etc.

(d) "Halo" includes chloro, bromo, fluoro and iodo and is preferably chloro, fluoro, or bromo.

The term "conventional readily removable carboxyl protecting group" refers to a known ester group which has been employed to block a carboxy group during the chemical reaction steps described below and which can be removed, if desired, by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation. Examples of such ester protecting groups include benzhydryl, allyl, p-nitrobenzyl, 2-naphthylmethyl, benzyl, trichloroethyl, silyl such as trimethylsilyl, phenacyl, p-methoxybenzyl, acetonyl, o-nitrobenzyl, 4-pyridylmethyl and t-butyl. Included within such protecting groups are those which are hydrolyzed under physiological conditions such as pivaloyloxymethyl, acetoxymethyl, phthalidyl, indanyl and methoxymethyl. A particularly advantageous carboxyl protecting group is p-nitrobenzyl which may be readily removed by catalytic hydrogenolysis.

The pharmaceutically acceptable salts referred to above include the nontoxic acid addition salts, e.g. salts with organic acids such as maleic, acetic, citric, succinic, benzoic, tartaric, fumaric, mandelic, ascorbic, lactic, gluconic and malic. Compounds of formula I in the form of acid addition salts may be written as

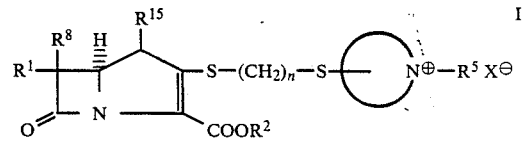

$R^2$=H or protecting group where $X^\ominus$ represents the acid anion. The counter anion $X^\ominus$ may be selected so as to provide pharmaceutically acceptable salts for therapeutic administration but, in the case of intermediate compounds of formula I, $X^\ominus$ may also be a toxic anion. In such a case the ion can be subsequently removed or substituted by a pharmaceutically acceptable anion to form an active end product for therapeutic use. When acidic or basic groups are present in the $R^1$ or $R^5$ group or on the

radical, the present invention may also include suitable base or acid salts of these functional groups, e.g. acid addition salts in the case of a basic group and metal salts (e.g. sodium, potassium, calcium and aluminum), the ammonium salt and salts with nontoxic amines (e.g. trialkylamines, procaine, dibenzylamine, 1-ephenamine, N-benzyl-β-phenethylamine, N,N'-dibenzylethylenediamine, etc.) in the case of an acidic group.

Compounds of formula I wherein $R^2$ is hydrogen, an anionic charge or a physiologically hydrolyzable ester group together with pharmaceutically acceptable salts thereof are useful as antibacterial agents. The remaining compounds of formula I are valuable intermediates which can be converted into the above-mentioned biologically active compounds.

The alkylene moiety, i.e., the group $(CH_2)_n$, is attached through the —S— atom via a ring carbon atom to an N-substituted quaternized aromatic heterocycle of the general formula

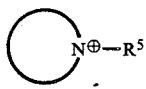

wherein the $R^5$ substituent is preferably an optionally substituted $C_1$-$C_6$ alkyl, $C_2$-$C_{10}$ alkenyl, $C_2$-$C_{10}$ alkynyl, $C_3$-$C_6$ cycloalkyl, $C_3$-$C_6$ cycloalkyl-$C_1$-$C_6$ alkyl, phenyl-$C_1$-$C_6$ alkyl, phenyl-$C_2$-$C_6$ alkenyl, phenyl-$C_2$-$C_6$ alkynyl, heteroaralkyl in which the alkyl moiety has 1–6 carbon atoms, heterocyclyl or heterocyclylalkyl ih which the alkyl moiety has 1–6 carbon atoms. The heteroaryl poriton of heteroaralkyl $R^5$ substituent may be a mono-, bi- or polycyclic aromatic heterocyclic group containing 1–4 O, N or S atoms; preferred are 5- or 6-membered heterocyclic rings such as thienyl and furyl. The heterocyclyl (or heterocyclyl portion of heterocyclylalkyl) $R^5$ substituent may be a mono-, bi- or polycyclic saturated or unsaturated non-aromatic heterocyclic group containing 1–4 O, N or S atoms; preferred are 5- or 6-membered heterocyclic rings such as tetrahydrothiophene, tetrahydrothiopyranne, tetrahydrofuran and tetrahydropyranne.

The $R^5$ substituent may be optionally substituted by 1–3 substituents independently selected from:

(a) $C_1$-$C_6$ alkyl optionally substituted by, preferably fluoro, chloro, carboxyl, hydroxy or carbamoyl groups;

(b) fluoro, chloro or bromo;

(c) —$OR^3$ (d) —$OCO_2R^3$;

(e) —$OCOR^3$;

(f) —$OCONR^3R^4$;

(g) 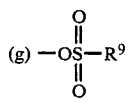

(h) —oxo;

(i) —$NR^3R^4$;

(j) $R^3CONR^4$—;

(k) —$NR^3CO_2R^4$;

(l) —$NR^3CONR^3R^4$;

(m) 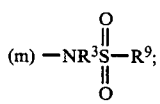

(n) —$SR^3$;

(o) —$SOR^9$;

(p) 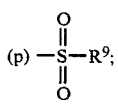

(q) —$SO_3R^3$;
(r) —$CO_2R^3$;
(s) —$CONR^3R^4$;
(t) —CN; or (u) phenyl optionally substituted by 1–3 substituents independently selected from fluoro, chloro, bromo, $C_1$-$C_6$ alkyl, —$OR^3$, —$NR^3R^4$, —$SO_3R^3$, or —$CONR^3R^3$, or —$CONR^3R^4$, wherein, relative to the above-named $R^5$ substituents, the groups $R^3$ and $R^4$ are independently selected from hydrogen; alkyl, alkenyl and alkynyl, having 1–10 carbon atoms; cycloalkyl, cycloalkylalkyl and alkylcycloalkyl, having 3–6 carbon atoms in the cycloalkyl ring and 1–6 carbon atoms in the aryl moieties; phenyl; aralkyl, aralkenyl and aralkynyl wherein the aryl moiety is phenyl and the aliphatic portion has 1–6 carbon atoms; and heteroaryl, heteroaralkyl, heterocyclyl and heterocyclylalkyl wherein the heteroaryl and heterocyclyl group or portion of a group is as defined above for $R^5$ and the alkyl moieties associated with said heterocyclic moieties have 1–6 carbon atoms; or $R^3$ and $R^4$ taken together with the nitrogen to which at least one is attached may form a 5 or 6-membered nitrogen-containing heterocyclic (as defined above for $R^5$) ring; and $R^9$ is as defined above for $R^3$ except that it may not be hydrogen. A most preferred $R^5$ substituent is $C_1$-$C_6$ alkyl, especially methyl.

In addition, the $R^5$ substituent, together with another ring atom of the

moiety, may form a fused heterocyclic or heteroaromatic ring, which ring may contain additional, preferably 1 or 2, hetero atoms selected from O, N and S. For example,

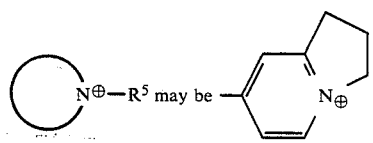

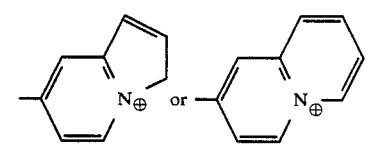

The group 

preferably represents a substituted or unsubstituted mono-, bi- or polycyclic aromatic heterocycle containing at least one nitrogen in the ring and 0–5 additional ring hetero atoms selected from O, S and N, said heterocyclic ring being attached to A through a ring carbon atoms and having a ring nitrogen atom quaternized by the group $R^5$.

The heteroaromatic

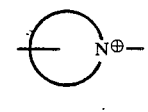

ring may be optionally substituted at available ring carbon atoms by preferably 1-5, most preferably 1-3, substituents independently selected from the group consisting of $C_1$-$C_4$ alkyl; $C_1$-$C_4$ alkyl substituted by, preferably 1-3, hydroxy, amino, $C_1$-$C_4$ alkylamino, di($C_1$-$C_4$)alkylamino, $C_1$-$C_4$ alkoxy, carboxy, halo (hereinafter intended to mean chloro, bromo, fluoro or iodo; preferably chloro, bromo or fluoro) or sulfo; $C_3$-$C_6$ cycloalkyl; $C_3$-$C_6$ cycloalkyl($C_1$-$C_4$)alkyl optionally substituted by 1-3 substituents mentioned above in connection with $C_1$-$C_4$ alkyl; $C_1$-$C_4$ alkoxy; $C_1$-$C_4$ alkylthio; amino; $C_1$-$C_4$ alkylamino; di($C_1$-$C_4$)alkylamino; halo; $C_1$-$C_4$ *alkanoylamino*; $C_1$-$C_4$ alkanoyloxy; carboxy; sulfo;

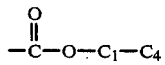

alkyl; hydroxy, amidino; guanidino; phenyl; phenyl substituted by 1-3 substituents independently selected from amino, halo, hydroxy, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo; phenyl($C_1$-$C_4$)-alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl or heteroaralkyl in which the hetero atom or atoms are selected from the group consisting of 1-4 O, S or N atoms and the alkyl moiety associated with heteroaralkyl has 1-6 carbon atoms, said heteroaryl and heteroaralkyl groups being optionally substituted in the heterocyclic ring moiety by 1-3 substituents independently selected from hydroxy, amino, halo, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo and in the alkyl moiety by 1-3 substituents selected from hydroxy, amino, $C_1$-$C_4$ alkylamino, di($C_1$-$C_4$)alkylamino, $C_1$-$C_4$ alkoxy, carboxy, halo and sulfo. In addition, available ring nitrogen atoms (other than the quaternized nitrogen) may be substituted by 1-3 substituents independently selected from the group consisting of $C_1$-$C_4$ alkyl; $C_1$-$C_4$ alkyl substituted by, preferably 1-3, hydroxy, amino, $C_1$-$C_4$ alkylamino, di($C_1$-$C_4$)-alkylamino, $C_1$-$C_4$ alkoxy, carboxy, halo or sulfo groups; $C_3$-$C_6$ cycloalkyl: $C_3$-$C_6$ cycloalkyl(-$C_1$-$C_4$)alkyl optionally substituted by 1-3 substituents mentioned above in connection with $C_1$-$C_4$ alkyl; phenyl; phenyl substituted by 1-3 substituents independently selected from amino, halo, hydroxy, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo; phenyl ($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl or heteroaralkyl in which the hetero atom or atoms are selected from the group consisting of 1-4 O, S or N atoms and the alkyl moiety associated with heteroaralkyl has 1-6 carbon atoms, said heteroaryl and heteroaralkyl groups being optionally substituted in the heterocyclic ring moiety by 1-3 substituents independently selected from hydroxy, amino, halo, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo and in the alkyl moiety by 1-3 substituents selected from hydroxy, amino, $C_1$-$C_4$ alkylamino, di($C_1$-$C_4$)alkylamino, $C_1$-$C_4$ alkoxy, carboxy, halo and sulfo. The most preferred ring carbon and nitrogen substituents are $C_1$-$C_4$ alkyl, especially methyl.

In a preferred embodiment, the group

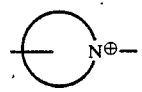

represents an aromatic 5- or 6- membered, N-containing heterocyclic ring containing 0-3 additional hetero atoms selected from O, S or N. Such aromatic heterocycle may, where possible, be fused to another ring which may be a saturated or unsaturated carbocyclic ring, preferably a $C_4$-$C_7$ carbocyclic ring, an aromatic carbocyclic ring preferably a phenyl ring, a 4-7 membered heterocyclic ring (saturated or unsaturated) containing 1-3 hetero atoms selected from O, S, N or $NR^{11}$ in which $R^{11}$ is hydrogen, $C_1$-$C_6$ alkyl optionally substituted by 1-2 substituents independently selected from $-OR^3$, $NR^3R^4$, $-CO_2R^3$, oxo, phenyl, fluoro, chloro, bromo, $SO_3R^3$ and $-CONR^3R^4$, or phenyl optionally substituted by 1-3 substituents independently selected from $C_1$-$C_6$ alkyl, $-OR^3$, $-NR^3R^4$, fluoro, chloro, bromo, $-SO_3R^3$, $-CO_2R^3$ and $-CONR^3R^4$ wherein $R^3$ and $R^4$ in such $R^{11}$ substituents are as defined above in connection with substituent $R^1$, or a 5-6 membered hetero-aromatic ring containing 1-3 hetero atoms selected from O, S, N or $R^{11}$ is as defined above. The 5- or 6-membered aromatic quaternized ring or, where appropriate, the carbocyclic, heterocyclic or heteroaromatic ring fused thereto, or both such rings, may be optionally substituted on available ring atoms by, preferably up to a total of five substituents for the total ring system, the substituents mentioned above in connection with the group

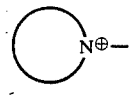

Still another preferred embodiment of the present invention comprises compounds of formula I wherein

represents a radical selected from the group consisting of

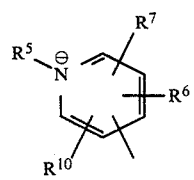

(a)

wherein $R^6$, $R^7$ and $R^{10}$ are independently selected from hydrogen; $C_1$-$C_4$ alkyl; $C_1$-$C_4$ alkyl substituted by, preferably 1-3, hydroxy, $C_1$-$C_4$ alkylamino di($C_1$-$C_4$ alkyl)amino, $C_1$-$C_4$ alkoxy, amino, sulfo, carboxy or halo (chloro, bromo, fluoro or iodo; preferably chloro, fluoro or bromo); $C_3-C_6$ cycloalkyl; $C_1-C_4$ alkoxy; $C_1-C_4$ alkylthio; amino; $C_1-C_4$ alkylamino; di($C_1-C_4$ alkyl)amino; halo (chloro, bromo, fluoro or iodo; preferably chloro, fluoro or bromo); $C_1-C_4$ alkylamino; $C_1-C_4$ alkanoyloxy; carboxy;

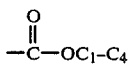

alkyl; hydroxy; amidino; guanidino; phenyl; phenyl substituted by one, two or three amino, halo (chloro, bromo, fluoro or iodo; preferably chloro, fluoro or bromo), hydroxy, trifluoromethyl, $C_1-C_4$ alkyl or $C_1-C_4$ alkoxy groups; phenyl ($C_1-C_4$)alkyl in which the phenyl portion may be optionally substituted by 1–3 substituents mentioned above in connection with phenyl and the alkyl portion may be optionally substituted by 1–3 substituents mentioned above in connection with $C_1-C_4$ alkyl; and heteroaryl and heteroaralkyl in which the hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms; or wherein two of $R^6$, $R^7$ or $R^{10}$ taken together may be a fused saturated carbocyclic ring, a fused aromatic carbocyclic ring, a fused non-aromatic heterocyclic ring or a fused heteroaromatic ring, said fused rings being optionally substituted by 1 or 2 of the substituents defined above for $R^6$, $R^7$ and $R^{10}$;

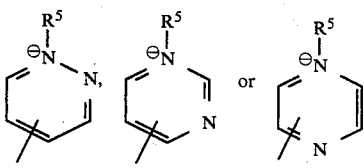

optionally substituted on a carbon atom by one to three substituents independently selected from $C_1-C_4$ alkyl; $C_1-C_4$ alkyl substituted by, preferably 1–3, hydroxy, $C_1-C_4$ alkylamino, sulfo, di($C_1-C_4$ alkyl)amino, $C_1-C_4$ alkoxy, amino, carboxy or halo (chloro, bromo, fluoro or iodo; preferably chloro, fluoro or bromo); $C_3-C_6$ cycloalkyl; $C_1-C_4$ alkoxy; $C_1-C_4$ alkylthio; amino; $C_1-C_4$ alkylamino; di($C_1-C_4$ alkyl)amino; halo (chloro, bromo, fluoro or iodo; preferably chloro, fluoro or bromo); $C_1-C_4$ alkanoylamino; $C_1-C_4$ alkanoyloxy; carboxy;

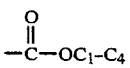

alkyl; hydroxy; amidino; guanidino; phenyl; phenyl substituted by one, two or three amino, halo (chloro, bromo, fluoro or iodo; preferably chloro, fluoro or bromo), hydroxyl, trifluoromethyl, $C_1-C_4$ alkyl or $C_1-C_4$ alkoxy groups; phenyl ($C_1-C_4$)alkyl in which the phenyl portion may be optionally substituted by 1–3 substituents mentioned above in connection with phenyl and the alkyl portion may be optionally substituted by 1–3 substituents mentioned above in connection with $C_1-C_4$ alkyl; and heteroaryl or heteroaralkyl in which hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms, or optionally substituted so as to form a fused carbocyclic, heterocyclic or heteroaromatic ring optionally substituted by 1 or 2 of the substituents defined above;

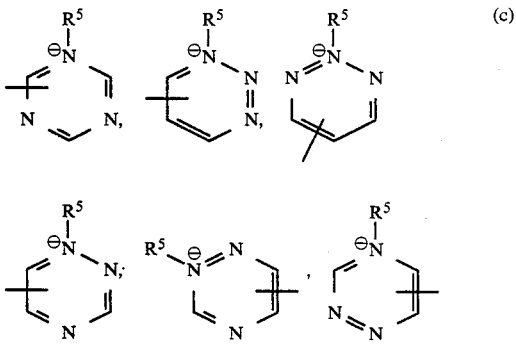

optionally substituted on a carbon atom by one or two substituents independently selected from $C_1-C_4$ alkyl; $C_1-C_4$ alkyl substituted by, preferably 1–3, hydroxy, $C_1-C_4$ alkylamino, sulfo, di($C_1-C_4$ alkyl)amino, $C_1-C_4$ alkoxy, amino, carboxy or halo (chloro, bromo, fluoro or iodo; preferably chloro, fluoro or bromo); $C_3-C_6$ cycloalkyl; $C_1-C_4$ alkoxy; $C_1-C_4$ alkylthio; amino; $C_1-C_4$ alkylamino; di($C_1-C_4$ alkyl)amino; halo (chloro, bromo, fluoro or iodo; preferably chloro, fluoro or bromo); $C_1-C_4$ alkanoylamino; $C_1-C_4$ alkanoyloxy; carboxy;

alkyl; hydroxy; amidino; guanidino, phenyl; phenyl substituted by one, two or three amino, halo (chloro, bromo, fluoro or iodo; preferably chloro, fluoro or bromo), hydroxyl, trifluoromethyl, $C_1-C_4$ alkyl or $C_1-C_4$ alkoxy groups; phenyl ($C_1-C_4$)alkyl in which the phenyl portion may be optionally substituted by 1–3 substituents mentioned above in connection with phenyl and the alkyl portion may be optionally substituted by 1–3 substituents mentioned above in connection with $C_1-C_4$ alkyl; an heteroaryl or heteroaralkyl in which the hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms, or optionally substituted so as to form a fused carbocyclic, heterocyclic or heteroaromatic ring optionally substituted by 1 or 2 of the substituents defined above;

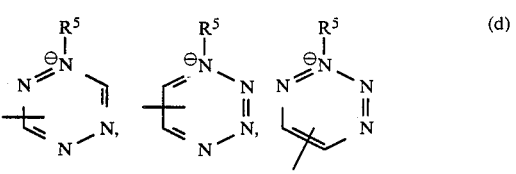

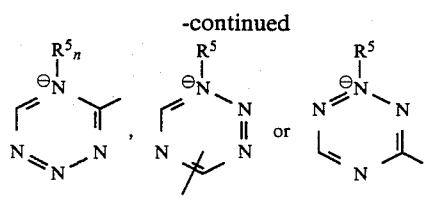

optionally substituted on a carbon atom by a substituent independently selected from $C_1$-$C_4$ alkyl; $C_1$-$C_4$ alkyl substituted by, preferably 1-3, hydroxy, $C_1$-$C_4$ alkylamino, di($C_1$-$C_4$ alkyl)amino, sulfo, $C_1$-$C_4$ alkoxy, amino, carboxy or halo (chloro, bromo, fluoro or iodo; preferably chloro, fluoro or bromo); $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo (chloro, bromo, fluoro or iodo; preferably chloro, fluoro or bromo); $C_1$-$C_4$ alkanoylamino; $C_1$-$C_4$ alkanoyloxy; carboxy;

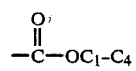

alkyl; hydroxy; amidino; guanidino, phenyl; phenyl substituted by one, two or three amino, halo (chloro, bromo, fluoro or iodo; preferably chloro, fluoro or bromo), hydroxyl, trifluoromethyl, $C_1$-$C_4$ alkyl or $C_1$-$C_4$ alkoxy groups; phenyl ($C_1$-$C_4$)alkyl in which the phenyl portion may be optionally substituted by 1-3 substituents mentined above in connection with phenyl and the alkyl portion may be optionally substituted by 1-3 substituents mentioned above in connection with $C_1$-$C_4$ alkyl; and heteroaryl or heteroaralkyl in which the hetero atom or atoms in the above-named heterocyclic moieties are selected from the group consisting of 1-4 oxygen, nitrogen or sulfur atoms and the alkyl moiety associated with said heteroaralkyl moiety has 1-6 carbon atoms;

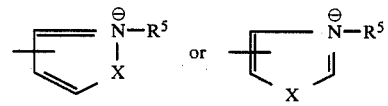

(e)

wherein X is O, S or NR in which R is $C_1$-$C_4$ alkyl; $C_1$-$C_4$ alkyl substituted by 1-3 hydroxy, amino, $C_1$-$C_4$ alkylamino, di($C_1$-$C_4$)-alkylamino, $C_1$-$C_4$ alkoxy, carboxy, halo or sulfo groups; $C_3$-$C_6$ cycloalkyl; $C_3$-$C_6$ cycloalkyl($C_1$-$C_4$)alkyl optionally substituted by 1-3 substituents mentioned above in connection with $C_1$-$C_4$ alkyl; phenyl; phenyl substituted by 1-3 substituents independently selected from amino, halo, hydroxy, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo; phenyl($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl and heteroalkyl in which the hetero atom or atoms are selected from the group consisting of 1-4 O, S or N atoms and the alkyl moiety associated with heteroaralkyl has 1-6 carbon atoms; said heteroaryl and heteroalkyl groups being optionally substituted in the heterocyclic ring moiety by 1-3 substituents independently selected from hydroxy, amino, halo, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo and in the alkyl moiety by 1-3 substituents selected from hydroxy, amino, $C_1$-$C_4$ alkylamino, di($C_1$-$C_4$)alkylamino, $C_1$-$C_4$ alkoxy, carboxy, halo and sulfo; said heteroaromatic radical being optionally substituted on a carbon atom by one or more substituents independently selected from $C_1$-$C_4$ alkyl; $C_1$-$C_4$ alkyl substituted by, preferably 1-3, hydroxy, amino, $C_1$-$C_4$ alkylamino, di($C_1$-$C_4$ alkyl)amino, $C_1$-$C_4$ alkoxy, sulfo, carboxy or halo (chloro, bromo, fluoro or iodo; preferably chloro, fluoro or bromo); $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo (chloro, bromo, fluoro or iodo; preferably chloro, fluoro or bromo); $C_1$-$C_4$ alkanoylamino; $C_1$-$C_4$ alkanoyloxy; carboxy;

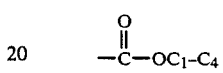

alkyl; hydroxy; amidino; guanidino; phenyl; phenyl substituted by one, two or three amino; halo (chloro, bromo, fluoro or iodo; preferably chloro, fluoro or bromo), hydroxyl, trifluoromethyl, $C_1$-$C_4$ alkyl or $C_1$-$C_4$ alkoxy groups; phenyl ($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl or heteroaralkyl in wgich the hetero atom or atoms in the above-named heterocyclic moieties are selected from the group consisting of 1-4 oxygen, nitrogen or sulfur atoms and the alkyl moiety associated with said hetero-aralkyl moiety has 1-6 carbon atoms, or optionally substituted so as to form a fused carbocyclic, heterocyclic or heteroaromatic ring optionally substituted by 1 or 2 of the substituents defined above;

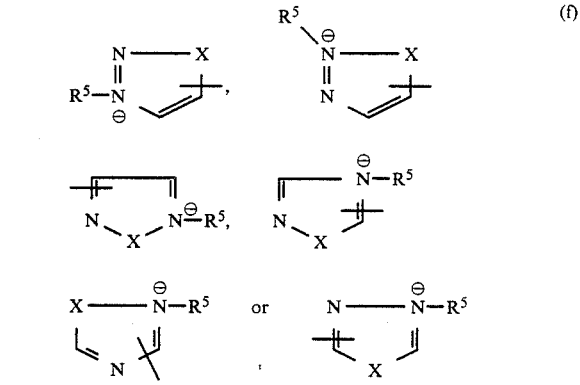

(f)

wherein X is O, S or NR in which R is $C_1$-$C_4$ alkyl; $C_1$-$C_4$ alkyl substituted by 1-3 hydroxy, amino, $C_1$-$C_4$ alkylamino, di($C_1$-$C_4$)alkylamino, $C_1$-$C_4$ alkoxy, carboxy, halo o sulfo groups; $C_3$-$C_6$ cycloalkyl; $C_3$-$C_6$ cycloalkyl($C_1$-$C_4$)alkyl optionally substituted by 1-3 substituents mentioned above in connection with $C_1$-$C_4$ alkyl; phenyl; phenyl substituted by 1-3 substituents independently selected from amino, halo, hydroxy, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo; phenyl($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl and heteroaralkyl in which the hetero atom or atoms are selected from the group consisting of 1-4 O, S or N atoms and the alkyl moiety associated with heteroaralkyl has 1-6 carbon atoms, said heteroaryl and heteroaralkyl groups being optionally substituted in the heterocyclic ring moiety by 1-3 substituents independently selected from hydroxy, amino, halo, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo and in the alkyl moiety by 1-3 substituents selected from hydroxy, amino, $C_1$-$C_4$ alkylamino, di($C_1$-$C_4$)alkylamino, $C_1$-$C_4$ alkoxy, carboxy, halo and sulfo; said heteroaromatic radial being optionally substituted on a carbon atom by a substituent selected from $C_1$-$C_4$ alkyl; $C_1$-$C_4$ alkyl substituted by, preferably 1-3, hydroxy, amino, $C_1$-$C_4$ alkylamino, di($C_1$-$C_4$ alkyl)amino, $C_1$-$C_4$ alkoxy, sulfo, carboxy or halo (chloro, bromo, fluoro or iodo; preferably chloro, fluoro or bromo); $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo (chloro, bromo, fluoro or iodo; preferably chloro, fluoro or bromo); $C_1$-$C_4$ alkanoylamino; $C_1$-$C_4$ alkanoyloxy; carboxy;

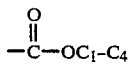

alkyl; hydroxy; amidino; guanidino; phenyl; phenyl substituted by one, two or three amino, halo (chloro, bromo, fluoro or iodo; preferably chloro, fluoro or bromo), hydroxyl, trifluoromethyl, $C_1$-$C_4$ alkyl or $C_1$-$C_4$ alkoxy groups; phenyl ($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl or heteroaralkyl in which hetero atom or atoms in the above-named heterocyclic moieties are selected from the group consisting of 1-4 oxygen, nitrogen or sulfur atoms and the alkyl moiety associated with said heteroaralkyl moiety has 1-6 carbon atoms; and

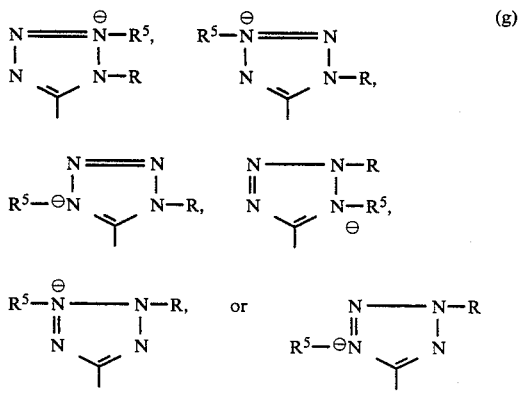

(g)

wherein R is $C_1$-$C_4$ alkyl; $C_1$-$C_4$ alkyl substituted by 1-3 hydroxy, amino, $C_1$-$C_4$ alkylamino, di($C_1$-$C_4$)alkylamino, $C_1$-$C_4$ alkoxy, carboxy, halo or sulfo groups; $C_3$-$C_6$ cycloalkyl $C_3$-$C_6$ cycloalkyl($C_1$-$C_4$)alkyl optionally substituted by 1-3 substituents mentioned above in connection with $C_1$-$C_4$ alkyl; phenyl; phenyl substituted by 1-3 substituents independently selected from amino, halo, hydroxy, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo; phenyl ($C_1$-$C_4$)alkyl in which the phenyl portion may be optionally substituted by 1-3 substituents mentioned above in connection with phenyl and the alkyl portion may be optionally substituted by 1-3 substituents mentioned above in connection with $C_1$-$C_4$ alkyl; and heteroaryl and heteroaralkyl in which the hetero atom or atoms are selected from the group consisting of 1-4 O, S or N atoms and the alkyl moiety associated with heteroaralkyl has 1-6 carbon atoms, said heteroaryl and heteroaralkyl groups being optionally substituted in the heterocyclic ring moiety by 1-3 substituents independently selected from hydroxy, amino, halo, trifluoromethyl, $C_1$-$C_4$ alkyl, $C_1$-$C_4$ alkoxy, $C_1$-$C_4$ alkylamino, di($C_1$-$C_4$)alkylamino, carboxy and sulfo and in the alkyl moiety by 1-3 substituents selected from hydroxy, amino, $C_1$-$C_4$ alkylamino, di($C_1$-$C_4$)alkylamino, $C_1$-$C_4$ alkoxy, carboxy, halo and sulfo. The R and $R^5$ groups may also be taken together to form a fused heterocyclic or heteroaromatic ring.

Particularly preferred are the compounds wherein $R^8$ is hydrogen, $R^1$ is

$R^{15}$ is hydrogen or methyl, $R^2$ is hydrogen or an anionic charge, and the group

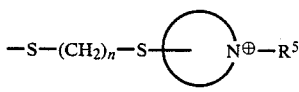

is

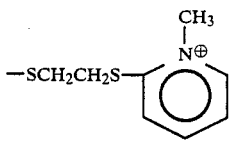

The carbapenem derivatives of general formula I are prepared from starting materials of the formula

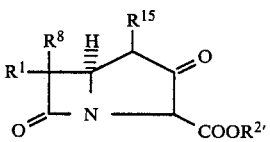

III wherein $R^1$, $R^8$ and $R^{15}$ are defined above and wherein $R^{2'}$ represents a conventional readily removable carboxy protected group. Compounds of formula II have been disclosed, for example, in Eurpoean Patent Application 38,869 (compound 7) and in Eurpoean Patent Application 54,917 and may be prepared by the general methods described therein.

The process for preparing compound I from starting materials III may be summarized by the following reaction scheme:

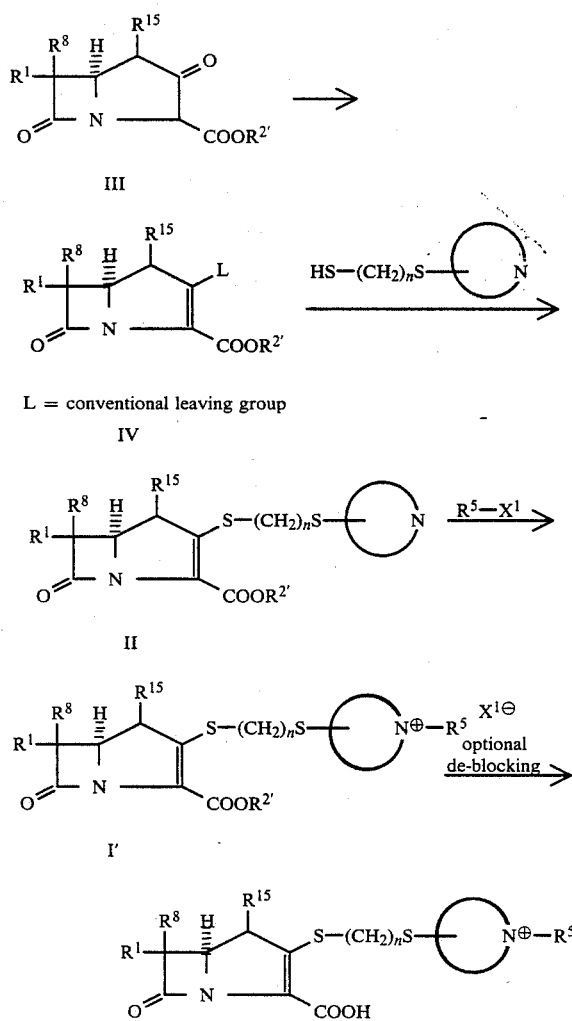

L = conventional leaving group

A variation of the above-described process is shown in the following reaction scheme:

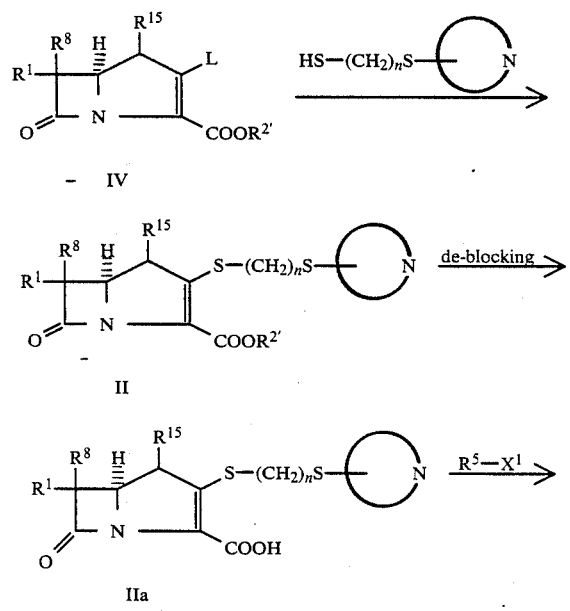

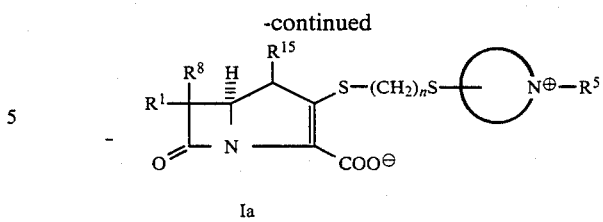

To elaborate on the above process, starting material III is reacted in an inert organic solvent such as methylene chloride, acetonitrile or dimethylformamide with about an equi-molar amount of an agent R°—L such as p-toluenesulfonic acid anhydride, p-nitrobenzene sulfonic acid anhydride, 2,4,6-triisopropylbenzenesulfonic acid anhydride, methanesulfonic acid anhydride, trifluoromethanesulfonic acid anhydride, diphenyl chlorophosphate, toluenesulfonyl chloride, p-bromobenzenesulfonyl chloride, or the like, wherein L is the corresponding leaving group such as toluenesulfonyloxy, p-nitrobenzenesulfonyloxy, diphenoxyphosphinyloxy, and other leaving groups which are established by conventional procedures and are well-known in the art. The reaction to establish the leaving group at the 2-position of intermediate III is advantageously carried out in the presence of a base such as diisopropylethylamine, triethylamine, 4-dimethylaminopyridine, or the like, at a temperature of from about $-20°$ to $+40°$ C., most preferably at about $0°$ C. The leaving group L of intermediate IV may also be halogen in which case such group is established by reacting intermediate III with a halogenating agent such as $\phi_3PCl_2$, $\phi PBr_2$, $(\phi O)_3PBr_2$, oxalylchloride or the like in a solvent such as $CH_2Cl_2$, $CH_3CN$, THF, or the like, in the presence of a base such as diisopropylethylamine, triethylamine, 4-dimethylaminopyridine, or the like. Intermediate IV may be isolated if desired, but is conveniently used for the next step without isolation or purification.

Intermediate IV is next converted to intermediate II by a conventional displacement reaction. Thus, intermediate IV may be reacted with approximately an equimolar amount of a heteroaralkyl mercaptan reagent of the formula

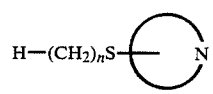

wherein

represents a mono-, bi- or polycyclic aromatic heterocyclic radical containing a quaternizable nitrogen in the ring, said ring being attached to the group HS—(CH$_2$)$_n$S— through a ring carbon atom, in an inert organic solvent such as dioxane, dimethylformamide, dimethylsulfoxide or acetonitrile and in the presence of a base such as diisopropylethylamine, triethylamine, sodium hydrogen carbonate, potassium carbonate or 4-dimethylaminopyridine. The temperature for the displacement is not critical, but an advantageous temperature range is from about $-40°$ C. to $25°$ C. Most conveniently, the reaction is carried out with cooling, e.g. at about 0° C. to −10° C.

Quaternization of the ring nitrogen in the heteroaralkyl group of intermediate II is carried out by reacting intermediate II in an inert organic solvent with at least an equivalent (up to about a 50 molar excess) of an alkylating agent of the formula

R⁵—X' wherein R⁵ is as defined above and X' is a conventional leaving group such as halo (chloro, bromo or iodo most preferably iodo) or a sulfonate ester moiety such as mesylate, tosylate or triflate. Examples of suitable non-reactive organic solvents are chloroform, methylene chloride, tetrahydrofuran, dioxane, acetone, dimethylsulfoxide and dimethylformamide. The temperature for the alkylation reaction is not critical and temperatures in the range of from about 0° C. to 40° C. are preferred. Most conveniently, the reaction step is carried out at room temperature.

The resultant intermediate I' will have a counter ion X' (e.g. derived from the alkylating agent used) associated with it which at this stage or at a later stage, i.e. following the de-blocking step, may be substituted by a different counter ion, e.g. one which is more pharmaceutically acceptable, by conventional procedures. Alternatively, the counter ion may be subsequently removed during the de-blocking step.

The de-blocking step to remove the carboxyl protecting group $R^{2'}$ of intermediate I' is accomplished by conventional procedures such as solvolysis, chemical reduction or hydrogenation. Where a protecting group such as p-nitrobenzyl, benzyl, benzyhydryl or 2-naphthylmethyl is used which can be removed by catalytic hydrogenation, intermediate I' in a suitable solvent such as dioxane-water-ethanol, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature of from 0° to 50° C. for from about 0.24 to 4 hours. When $R^2$ is a group such as o-nitrobenzyl, photolysis may also be used for deblocking. Protecting groups such as 2,2,2-trichloroethyl may be removed by mild zinc reduction. The ally protecting group may be removed with a catalyst comprising a mixture of a palladium compound and triphenylphosphine in a mixture of a palladium compound and triphenylphosphine. in an aprotic solvent such as tetrahydrofuran, diethyl ether or methylene chloride. Similarly, other conventional carboxyl protecting groups may be removed by methods known to those skilled in the art. Finally, as mentioned above, compounds of formula 1' where $R^{2'}$ is a physiologically hydrolyzable ester such as acetoxymethyl, phthalidyl, indanyl, pivaloyloxymethyl, methoxymethyl, etc. may be administered directly to the host without de-blocking since such esters are hydrolized in vivo under physiological conditions.

It will be understood that where the $R^1$, $R^8$, $R^5$ or $R^{15}$ substituent or the heteroaromatic ring attached to $(CH_2)_nS$ contain a functional group which might interfere with the intended course of reaction, such group may be protected by a conventional blocking group and then subsequently deblocked to regenerate the desired functional group. Suitable blocking groups and procedures for introducing and removing such groups are well known to those skilled in the art.

In a variant of the above process, the carboxyl protecting group of intermediate II may be removed prior to the quaternization step. Thus, the carboxyl protecting group is removed as described above to give the corresponding free carboxylic acid and the free acid is then quaternized with alkylating agent $R^5$—X' to give the desired quaternized product of formula I. When the de-protected intermediate IIa is quaternized, the solvent may be a non-reactive organic solvent. Examples of suitable solvents include water, organic solvents such as chloroform, methylene chloride, tetrahydrofuran, dioxane, acetone, dimethylsulfoxide and dimethylformamide and water-organic solvent mixtures such as water-acetone or water-dimethylformamide. The temperature for the quarternization of intermediate IIa is not critical and temperatures in the range of from about −40° C. to about room temperature may be conveniently employed. Most advantageously, the reaction is carried out at about 0° C.

When deprotected intermediate IIa is obtained as a carboxylate salt, it is desirable to add a strong acid such as toluenesulfonic acid to generate the free carboxylic acid prior to quaternization. This is found to greatly facilitate the preferential quaternization of the ring nitrogen.

In another process for preparation of compounds of formula I, an intermediate of the formula

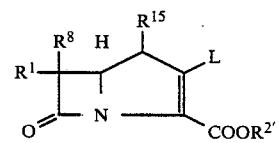

wherein $R^1$, $R^8$ and $R^{15}$ are as defined above, $R^{2'}$ is a conventional readily removable carboxyl protecting group and L is a conventional leaving group such as toluenesulfonyloxy, p-nitrobenzenesulfonyloxy, diphenoxyphosphinyloxy or halo is reacted with a thiol compound of the formula

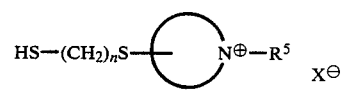

wherein n and

are as defined above and $X^\ominus$ is a counter anion in an inert solvent and in the presence of base to produce a carbapenem product of the formula

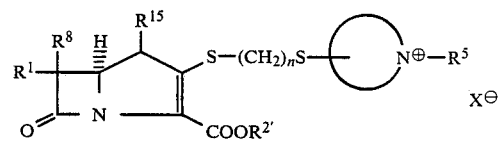

wherein $R^1$, $R^8$, $R^{2'}$ $R^{15}$, n,

and X⊖ are as defined above and, if desired, the carboxyl protecting group $R^{2'}$ is removed as previously described to give the corresponding de-blocked compound of formula I, or a pharmaceutically acceptable salt thereof.

The alternative process utilizes the intermediate of the formula

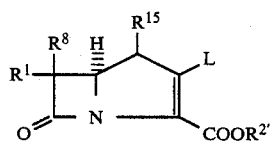

which, as mentioned before, has been disclosed, for example, in European Patent Applications 38,869 and 54,917 and which may be prepared by the general methods described therein. L represents a conventional leaving group (defined as "X" in European Patent Application 38,869) such as chloro, bromo, iodo, benzenesulfonyloxy, p-toluenesulfonyloxy, p-nitrobenzenesulfonyloxy, methanesulfonyloxy, trifluoromethanesulfonyloxy, diphenoxyphosphinyloxy or di(trichloroethoxy)phosphinyloxy. The preferred leaving group is diphenoxyphosphinyloxy.

Intermediates of formula IV are generally formed in situ by reacting an intermediate of the formula

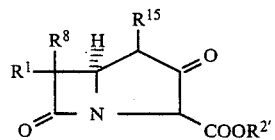

wherein $R^1$, $R^8$, $R^{15}$ and $R^{2'}$ are as defined above with a suitable acylating agent $R^0$—L. The preferred intermediate IV where L is diphenoxyphosphinloxy may be prepared by reacting keto ester III in an inert organic solvent such as methylene chloride, acetonitrile or dimethylformamide with about an equimolar amount of diphenyl chlorophosphate in the presence of a base such as diisopropylethulamine, triethylamine, 4-dimethylaminopyridine or the like at a temperature of from about $-20°$ C. to $+40°$ C., most preferably at about $0°$ C. Intermediate IV may be isolated, if desired, but is conveniently used as the starting material for the alternative process without isolation or purification.

Carbapenem intermediate IV is reacted with a quaternary amine thiol compound of the formula

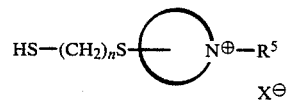

wherein

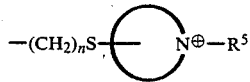

is as defined above and X⊖ is a counter anion. The reaction is carried out in an inert solvent such as acetonitrile, acetonitrile-dimethylformamide, tetrahydrofuran, tetrahydrofuran-H₂O, acetonitrile-H₂O or acetone in the presence of base. The nature of the base is not critical. Suitable bases include sodium hydroxide, diisopropylethylamine, 1,8-diazabicyclo[5.4.0]undec-7-ene, 1,5-diazabicyclo[4.3.0]non-5-ene and tri($C_1$-$C_4$)alkylamines such as triethylamine, tributylamine or tripropylamine. Reaction of intermediate IV and thiol VII may be carried out over a wide temperature range, e.g. $-15°$ C. up to room temperature, but is preferably done at a temperature in the range of from about $-15°$ C. to $+15°$ C., most preferably at around $0°$ C.

The carbapenem product produced by reaction of the quaternary amine thiol VII with intermediate IV will have a counter anion associated with it [e.g. $(C_6H_5O)_2PO_2^-$, $Cl^-$ or the anion associated with the quaternary thiol] which may at this stage be substituted by a different counter anion, e.g. one which is more pharmaceutically acceptable, by conventional procedures. Alternatively, the counter anion may be removed during the subsequent de-blocking step. Where the quaternized carbapenem compound and counter anion form an insoluble product, the product may crystallize out as it is formed and be collected pure by filtration.

Following formation of the desired carbapenem product, the carboxyl protecting group $R^{2'}$ of intermediate I' may be optionally removed by conventional procedures such as solvolysis, chemical reduction of hydrogenation. Where a protecting group such as p-nitrobenzyl, benzyl, benzhydryl or 2-naphthylmethyl is used which can be removed by catalytic hydrogenation, intermediate I' in a suitable solvent such as dioxane-water-ethanol, tetrahydrofuran-diethylether-buffer, tetrahydrofuran-aqueous dipotassium hydrogen phosphateisopropanol or the like may be treated under a hydrogen pressure of from 1 to 4 atmospheres in the presence of a hydrogenation catalyst such as palladium on charcoal, palladium hydroxide, platinum oxide or the like at a temperature of from $0°$ to $50°$ C. or from about 0.24 to 4 hours. When $R^{2'}$ is a group such as o-nitrobenzyl, photolysis may also be used for deblocking. Protecting groups such as 2,2,2-trichloroethyl may be removed by mild zinc reduction. The allyl protecting group may be removed by using a catalyst comprising a mixture of a palladium compound and triphenyl phosphine in a suitable aprotic solvent such as tetrahydrofuran, methylene chloride or diethyl ether. Similarly, other conventional carboxyl protecting groups may be removed by methods known to those skilled in the art. Finally, as mentioned above, compounds of Formula I' where $R^{2'}$ is a physiologically hydrolyzable ester such as acetoxymethyl, phthalidyl, indanyl, pivaloyloxymethyl, methoxymethyl, etc., may be administered directly to the host without de-blocking since such esters are hydrolyzed in vivo under physiological conditions.

The thiol intermediates of Formula VII may be prepared, for example, by reacting a dithiol of the formula HS(CH₂)ₙSH with a compound of the formula

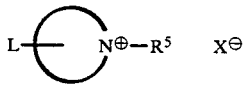

wherein L is a leaving group as defined above, n and

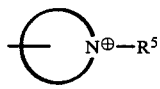

are as defined above and $X^{\ominus}$ is a counter ion. The reaction is carried out under the same conditions previously described for the reaction of Compounds IV and VII.

As in the case of other β-lactam antibiotics, compounds of general formula I may be converted by known procedures to pharmaceutically acceptable salts which, for purposes of the present invention, are substantially equivalent to the non-salted compounds. Thus, for example, one may dissolve a compound of formula I wherein $R^2$ is an anionic charge in a suitable inert solvent and then add an equivalent of a pharmaceutically acceptable acid. The desired acid addition salt may be recovered by conventional procedures, e.g., solvent precipitation, lyophilization, etc. Where other basic or acidic functional groups are present in the compound of formula I, pharmaceutically acceptable base addition salts and acid addition salts may be similarly prepared by known methods.

It will be appreciated that certain products within the scope of formula I may be formed as optical isomers as well as epimeric mixtures thereof. It is intended that the present invention include within its scope all such optical isomers and epimeric mixtures. For example, when the 6-substituent is hydroxyethyl, such substituent may be in either the R or S configuration and the resulting isomers as well as epimeric mixtures thereof are encompassed by the present invention.

A compound of formula I where $R^2$ is hydrogen or an anionic charge, or a pharmaceutically acceptable salt thereof may also be converted by conventional procedures to a corresponding compound where $R^2$ is a physiologically hydrolyzable ester group, or a compound of formula I wherein $R^2$ is a conventional carboxyl protecting group may be converted to the corresponding compound where $R^2$ is hydrogen, an anionic charge or a physiologically hydrolyzable ester group, or a pharmaceutically acceptable salt thereof.

The novel carbapenem derivatives of general formula I wherein $R^2$ is hydrogen, an anionic charge or a physiologically hydrolyzable carboxy protecting group, or the pharmaceutically acceptable salts thereof, are potent antibiotics active against various gram-positive and gram-negative bacteria and they may be used, for example, as animal feed additives for promotion of growth, as preservatives in food, as bactericides in industrial applications, for example in water based paint and in the white water of paper mills to inhibit the growth of harmful bacteria, and as disinfectants for destroying or inhibiting the growth of harmful bacteria on medical and dental equipment. They are especially useful, however, in the treatment of infectious disease in humans and other animals caused by gram-positive or gram-negative bacteria.

The pharmaceutically active compounds of this invention may be used alone or formulated as pharmaceutical compositions comprising, in addition to the active carbapenem ingredient, a pharmaceutically acceptable carrier or diluent. The compounds may be administered by a variety of means; those of principal interest include; orally, topically or parenterally (e.g., intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain formulatory agents such as suspending, stabilizing and dispersing agents. The compositions may be in ready to use form or in powder form for reconstitution at the time of delivery with a suitable vehicle such as sterile water.

The dosage to be administered depends to a large extent on the particular compound being used, the particular composition formulated, the route of administration, the nature and condition of the host and the particular situs and organism being treated. Selection of the particular preferred dosage and route of application, then, is left to the discretion of the therapist. In general, however, the compounds may be administered parenterally or orally to mammalian hosts in an amount of from about 5 to 200 mg/kg/day. Administration is generally carried out in divided does, e.g., three or four times a day.

To illustrate the potent broad-spectrum antibacterial activity of the carbapenems of the present invention, both in vitro and in vivo, and the low toxicity of the compounds, biological data is provided below rating to the presently preferred carbapenem compound of the present invention.

In Vitro Activity

Samples of the carbapenem compound prepared in Example 1 after solution in water and dilution with Nutrient Broth were found to exhibit the following Minimum Inhibitory Concentrations (M.I.C.) in mcg/ml versus the indicated microorganisms as determined by overnight incubation at 37° C. by tube dilution.

| In Vitro Antibacterial Activity of Carbapenem Derivative of Example 1 | | |
| --- | --- | --- |
| Organism | MIC (mcg/ml) New Compound | PD$_{50}$ I.M. |
| Str. pneumoniae | 0.0005 | |
| Str. pyogenes | 0.0005 | |
| Staph. aureus | 0.004 | |
| Staph. aureus + 50% serum | 0.008 | |
| Staph. aureus (Pen-R) | 0.004 | |
| Str. faecalis | 0.13 | |
| E. coli | 0.008 | |
| E. coli | 0.016 | |
| K. pneumoniae | 0.03 | |
| K. pneumoniae | 0.06 | |
| Pr. mirabilis | 0.016 | |
| Pr. vulgaris | 0.016 | |
| Pr. morganii | 0.06 | |
| Pr. rettgeri | 0.13 | |
| Ser. marcescens | 0.03 | |
| Ent. cloacae | 0.06 | |
| Ent. cloacae | 0.13 | |
| Ps. aeruginosa | 8 | 2.9 |
| Ps. (Carb-R) | 2 | |

In Vivo Activity

The in vivo therapeutic efficacy of the compound of Example 1 after intramuscular administration to mice experimentally infected with various organisms are shown in the following Table. The $PD_{50}$ (dose in mg/kg required to give protection to 50% of the infected mice) is indicated.

| Protective Effect in the Intramuscular Treatment of Infected Mice | |
|---|---|
| Organism | $PD_{50/Treatment}$ (mg/kg) Compound of Example 1 |
| *Ps. aeruginosa* | 2.9 |

Treatment Schedule: Mice were treated i.m. with drugs 0 and 2 hours post-infection.

Blood Levels in Mice After Intramuscular Administration

Blood levels and the half-life of the compound of Example 1 after intramuscular administration of 20 mg/kg in mice are shown in the Table below.

| | Minutes after Administration | | | | | | (min.) | (μg.h/ml) |
|---|---|---|---|---|---|---|---|---|
| Compound | 10 | 20 | 30 | 45 | 60 | 90 | *t½ | **AUC |
| | Blood Level (μg/ml) | | | | | | | |
| Compound of Example 1 | 11.1 | 8 | 3.6 | 1 | <0.3 | <0.3 | 8 | 4.1 |

Urinary Recovery

The Urinary recovery of the compound of Example 1 after intramuscular administration (20 mg/kg) to mice is shown in the following Table.

| Urinary Recovery Intramuscular Administration of 20 mg/kg to Mice Percentage of Dose Recovered | |
|---|---|
| Compound | 0-24 Hours After Administration |
| Compound of Example 1 | 31.5 |

Compounds were solubilized in 0.1 M phosphate buffer pH 7. Values are from a single test; 4 mice per compound.

The following examples illustrate but do not limit the scope of the present invention.

EXAMPLE 1

PREPARATION OF (5R,6S) 6-(1R-hydroxyethyl)-3-[(1-methylpyridinium-2-yl)-2-thioethylthio]-7-oxo-1-azabicyclo(3.2.0)hept-2-ene-2-carboxylate A. 2-(2-mercaptoethylthio)-1-methylpyridinium iodide and/or fluoride

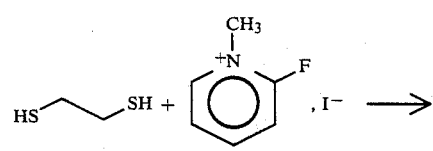

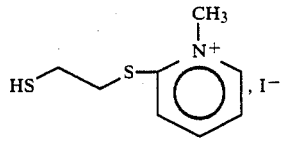

To a mixture of 1,2-ethanedithiol (0.63 mL, 7.5 mmol), water (21 mL) and tetrahydrofuran (4 mL) were added simultaneously 2-fluoro-1-methylpyridinium iodide, described by G. B. Barlin and J. A. Benbow, J.C.S. Perkin II, 790 (1974), (0.90 g, 3.72 mmol) and 1N sodium hydroxide solution (5-6 mL) to keep the pH of the mixture between 6 and 7. When the addition of 2-fluoro-1-methylpyridinium iodide was completed, the reaction mixture was stirred at 23° C. while the pH was kept at 7.1 by the addition of the 1N sodium hydroxide solution. When the pH of the mixture was stabilized at 7.1, the solvents were evaporated under high vacuum until dryness. The solid was triturated in ether (3×10 mL) and in acetonitrile (2×8 mL). The ether solution was dried (MgSO4) and concentrated to give 0.10 g of N-methyl-2(1H)-pyridothione. The acetonitrile solution was dried (MgSO4) and concentrated to give 0.74 g of 2-(2-mercaptoethylthio)-1-methylpyridinium iodide and/or fluoride mixed with some inorganic salts; ir (KBr) $\nu_{max}$: 1617 (pyridinium) cm$^{-1}$, $^1$Hmr (DMSO-d$_6$) δ: 2.75-3.1 (m, 2H, C$\underline{H}_2$SH), 3.4-3.9 (m, CH$_2$S and SH), 4.17 (s, 3H, CH$_3$ on pyridinium), 7.6-9.2 (m, 4H, H's of pyridinium). The acetonitrile insoluble material (0.38 g) was 1,2-di(1-methylpyridinium-2-thio)ethane diiodide or/and difluoride or monoiodidemonofluoride mixed with some inorganic salts; $^1$Hmr (DMSO-d$_6$) δ: 3.90 (4H, s, SCH$_2$CH$_2$S), 4.21 (6H, s, CH$_3$'s on pyridinium), 7.7-9.1 (8H, m, H's of pyridiniums). The thiol was used without any further purification.

B. (5R,6S) 6-(1R-hydroxyethyl)-3-[(1-methylpyridinium-2-yl)-2-thioethylthio]-7-oxo-1-azabicyclo(3.2.0)hept-2-ene-2-carboxylate

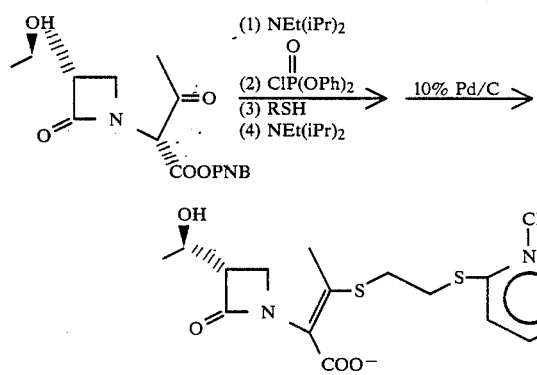

To a cold (0°C.) solution of (5R,6R) paranitrobenzyl 6-(1R-hydroxyethyl)-3,7-dioxo-1-azabicyclo(3.2.0)heptane-2R-carboxylate (0.624 g, 1.79 mmol) in acetonitrile (7 mL) kept under nitrogen atmosphere was added diisopropylethylamine (0.374 mL, 2.15 mmol) and diphenyl chlorophosphate (0.446 mL, 2.15 mmol). The reaction mixture was stirred for 30 minutes and treated with a suspension of crude 2-(2-mercaptoethylthio)-1-methylpyridinium iodide and/or fluoride (1.2 g) in a mixture of acetonitrile (6.5 mL) and water (1.1 mL), and dropwise (10 minutes) with diisopropylethylamine (0.374 mL, 2.15 mmol). After stirring for 1.25 hours at 5° C., cold water (40 mL) was added. The resulting solution was chromatographed on PrepPak-500/C$_{18}$ (Waters Associates) column (3.5×9 cm) with 25–40% acetonitrile in water as eluting solvents to give a yellowish powder (0.60) g) after lyophilization. To a solution of that powder in tetrahydrofuran (31 mL) and potassium phosphate monobasic-sodium hydroxide buffer (0.15M, pH 7.22) mixture was added ether (31 mL) and 10% palladium on charcoal (0.58 g). The resulting mixture was hydrogenated at 23° C. under 40 psi for 1 hour and filtered on a Celite pad. The two phases were separated and the organic phase was extracted with buffer (2×10 mL). The aueous phases were combined, washed with ether (2×20 mL), concentrated to 20 mL under vacuum and chromatographed on Prep-Pak-500/C$_{18}$ column (3.5×12 cm) with 0–4% acetonitrile in water as eluting solvent to give 0.16 g of product after lyophilization. The compound was repurified to HPLC ($\mu$-bondapak C$_{18}$) to give 0.078 g (11%) after lyophilization; ir (KBr) $\nu_{max}$: 3000–3700 (OH), 1750 (C—0 of $\beta$-lactam), 1610 (pyridinium), 1588 (carboxylate) cm$^{-1}$, $^1$Hmr (D$_2$0) δ: 1.23 (d, J 6.3 Hz, 3H, C$\underline{H}_3$CHOH), 2.8–3.5 (m, 6H, H-6, H-$\underline{4}$, H-5, C$\underline{H}_2$S-pyridinium), 3.5–3.8 (m, 2H, SC$\underline{H}_2$CH$_2$S pyridinium), 4.17 (s, CH$_3$ on pyridinium), 3.9–$\underline{4}$.4 (m, CH$_3$C$\underline{H}$OH), 7.4–8.7 (m, 4H, H's of pyridinium); uv (H$_2$O) $\lambda_{max}$: 248 ($\epsilon$4187), 309 ($\epsilon$10336): [$\alpha$]$_D^{23}$ 6.6° (c 0.37, H$_2$O).

EXAMPLE 2

Following the general procedures of Example 1, the following carbapenem products are made by using the intermediate of the formula.

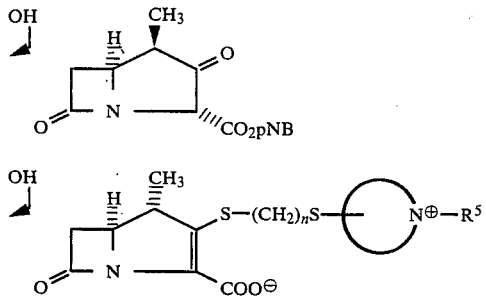

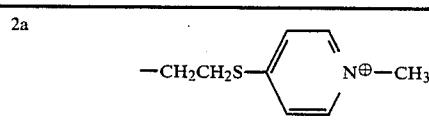

| Example No. | —(CH$_2$)$_n$S— | N$^{\oplus}$—R$^5$ |
|---|---|---|
| 2a | —CH$_2$CH$_2$S— | <image of N-methylpyridinium> |
| 2b | —CH$_2$CH$_2$S— | <image of N-methylpyridinium> |
| 2c | —CH$_2$CH$_2$S— | <image of dimethyl pyridinium with CH$_3$> |
| 2d | —CH$_2$CH$_2$S— | <image of triazolium N-CH$_3$, N$^{\oplus}$—CH$_3$> |
| 2e | —CH$_2$CH$_2$S— | <image of imidazolium with CH$_3$> |
| 2f | —CH$_2$CH$_2$S— | <image of thiazolium with CH$_3$> |
| 2g | —CH$_2$CH$_2$S— | <image of imidazolium di-CH$_3$> |
| 2h | —CH$_2$CH$_2$S— | <image of N=N$^{\oplus}$—CH$_3$, S> |
| 2i | —CH$_2$CH$_2$CH$_2$S— | <image of N-methylpyridinium> |

What is claimed is:
1. A compound of the formula

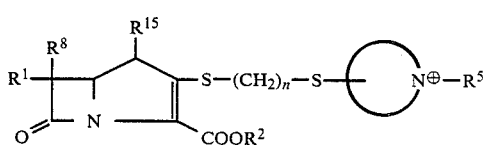

wherein R$^8$ is hydrogen and R$^1$ is hydroxyethyl; R$^5$ is C$_1$-C$_6$ alkyl; R$^{15}$ is hydrogen or methyl; n is an integer of 1, 2 or 3; R$^2$ is hydrogen, an anionic charge or a conventional readily removable carboxyl protecting group, provided that when R$^2$ is hydrogen or a protecting group, there is also present a counter ion; and

represents an aromatic 5- or 6-membered N-containing heterocyclic ring containing 0–3 additional hetero atoms selected from O, S or N, said aromatic ring being optionally substituted at available ring carbon or nitrogen atoms by $C_1$–$C_4$ alkyl substituents, and said ring being attached to S through a ring carbon atom and having a ring nitrogen which is quaterized by the group $R^5$; or a pharmaceutical acceptable salt thereof.

2. A compound of the formula

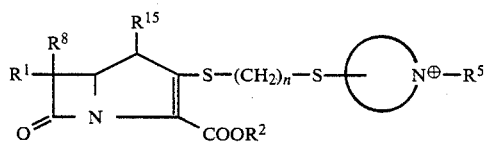

wherein $R^8$ is hydrogen and $R^1$ is hydroxyethyl; $R^{15}$ is hydrogen or methyl; n is an integer of 1, 2 or 3; $R^2$ is hydrogen, an anionic charge or a conventional readily removable carboxyl protecting group, provided that when $R^2$ is hydrogen or a protecting group, there is also present a counter ion; and

represents a group of the formula

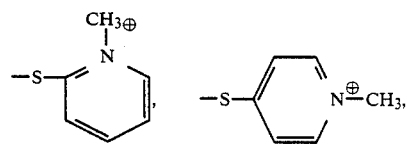

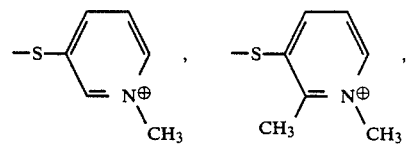

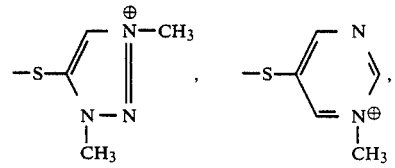

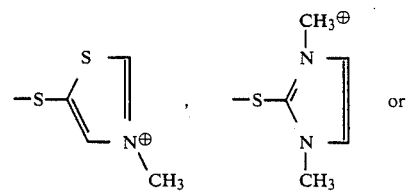

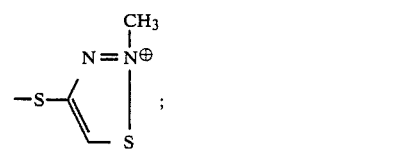

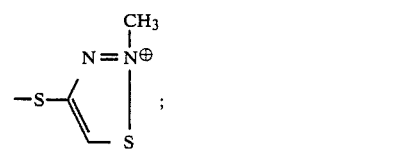

or pharmaceutically acceptable salt

3. A compound as defined in claim 1 or claim 2 wherein $R^2$ is hydrogen or an anionic charge.

4. (5R,6S) 6-(1R-hydroxyethyl)-3-[(1-methylpyridinium-2-yl)-2-thioethylthio]-7-oxo-1-azabicyclo (3.2.0)hept-2-ene-2-carboxylate.

5. (4R,5R,6S) 6-(1R-hydroxyethyl)-4-methyl-3-[(1-methylpyridinium-2-yl)-2-thioethylthio]-7-oxo-1-azabicyclo (3.2.0) hept-2-ene-2-carboxylate.

* * * * *